United States Patent [19]

Klages et al.

[11] Patent Number: 5,100,782
[45] Date of Patent: Mar. 31, 1992

[54] PROCESS FOR THE PREPARATION OF L-AMINO ACIDS AND AMINO ACID AMIDES

[75] Inventors: Uwe Klages; Alfred Weber, both of Berlin, Fed. Rep. of Germany

[73] Assignee: Schering Aktiengesellschaft, Berlin and Bergkamen, Fed. Rep. of Germany

[21] Appl. No.: 458,648

[22] PCT Filed: Apr. 13, 1989

[86] PCT No.: PCT/DE89/00232

§ 371 Date: Jan. 5, 1990

§ 102(e) Date: Jan. 5, 1990

[87] PCT Pub. No.: WO89/10969

PCT Pub. Date: Nov. 16, 1989

[30] Foreign Application Priority Data

May 6, 1988 [DE] Fed. Rep. of Germany ....... 3816063

[51] Int. Cl.$^5$ .................. C12P 13/02; C12P 13/04; C12P 39/00; C12P 41/00
[52] U.S. Cl. ................... 435/42; 435/106; 435/108; 435/110; 435/113; 435/114; 435/115; 435/250
[58] Field of Search ............... 435/42, 106, 108, 110, 435/113-115, 280

[56] References Cited

U.S. PATENT DOCUMENTS

| | | | |
|---|---|---|---|
| 4,080,259 | 3/1978 | Boesten et al. | 435/280 |
| 4,276,380 | 6/1981 | Yukawa et al. | 435/115 |
| 4,366,250 | 12/1982 | Jallageas et al. | 435/280 |
| 4,427,774 | 1/1984 | Yukawa et al. | 435/115 |
| 4,705,752 | 11/1987 | Boesten et al. | 435/106 |
| 4,812,403 | 3/1989 | Boesten et al. | 435/280 |
| 4,847,412 | 7/1989 | Boesten et al. | 548/344 |
| 4,880,737 | 11/1989 | Kerkhoffs et al. | 435/280 |
| 4,918,196 | 4/1990 | Doya et al. | 548/205 |

OTHER PUBLICATIONS

Derwent Abs. 86-346609/52, Godtfredse et al, WO8607386 (Dec. 1986).
Derwent Abs. 90-227356/30, J02154692, Ashai Chem. 6-1990.
Derwent Abs. 87-025758/07 J61282087, Asahi Chem. 12-86.

*Primary Examiner*—Herbert J. Lilling
*Attorney, Agent, or Firm*—Millen, White & Zelano

[57] ABSTRACT

The disclosure relates to a process for the preparation of L-amino acids of general Formula I $$A-\underset{\underset{NH_2}{|}}{CH}-COOH \qquad (I)$$

wherein A means the residue of an amino acid molecule,
from D,L-aminonitriles of general Formula II $$A-\underset{\underset{NH_2}{|}}{CH}-CN \qquad (II)$$

wherein A has the meaning given above,
characterized by fermenting the α-aminonitriles with a culture of Actinetobacter calcoaceticus DSM 3875 and reacting the thus-obtained D,L-amino acid amides of general Formula III $$A-\underset{\underset{NH_2}{|}}{CH}-CONH_2 \qquad (III)$$

wherein A has the meaning given above,
with a culture of a microorganism containing amino acid amide racemases and L-amino acid amide amidases.

4 Claims, No Drawings

PROCESS FOR THE PREPARATION OF L-AMINO ACIDS AND AMINO ACID AMIDES

The invention relates to the process for the preparation of L-amino acids and amino acid amides as characterized in the claims.

Processes for the fermetative production of L-amino acids from D,L-α-aminonitriles are conventional (European Patent Application 23214). In these previously known methods, the L-form of the α-aminonitrile is hydrolyzed to the L-amino acid whereas the o D-form of the α-aminonitrile either is not hydrolyzed at all or is hydrolyzed merely to the D-amino acid amide. As a consequence thereof, the conventional methods theoretically allow only yields of 50%.

It has now been found hat certain micro-organisms not only possess L-amino acid amide amidases but moreover also contain amino acid amide racemases which racemize the D-amino acid amides to D,L-α-amino acid amides. These microorganisms thus have the capability to convert also the D-form of the D,L-α-amino acid amides into L-amino acids. Finding such micro-organisms does not present any difficulties to one skilled in the art. Various microorganisms are tested by means of the usual screening methods whether they show the capability of converting D-amino acid amides into L-amino acids. Previously known micro-organisms possessing this capability to an excellent degree are, in accordance with investigations conducted in-house, Arthrobacter sp. ATCC 31 652 and Corynebacterium sp. ATCC 31 662.

It has furthermore been found that micro-organisms exist having the capability of converting α-aminonitriles into amino acid amides without hydrolyzing them further. A microorganism has been isolated from soil samples which has the capability of splitting D,L-α-amino-β-phenylpropionitrile to phenylalanine.

This microorganism has the following taxonomic properties:

| Colony morphology | round, smooth-edged, translucent, slimy |
| --- | --- |
| Cytomorphology | immobile, short rods length 1.5-2.5 μm, width 1 μm |
| Gram stain | Gram-negative |
| Endospores | negative |
| Catalase | positive |
| Cytochrome-C oxidases | negative |
| Citrate use | positive |
| Nitrite from nitrate | negative |
| Voges-Proskauer | negative |
| Methyl red | negative |
| Indole formation | negative |
| Urease | positive |
| $H_2S$ formation | negative |
| Use of sugar | acid from glucose, no acid from sucrose, fructose, lactose, maltose, mannitol, glycerol, no gas formation |

Based on its morphological and physiological properties, the microorganism was identified as Actinetobacter calcoaceticus in accordance with the criteria of "Bergey's Manual of Determinative Bacteriology".

This microorganism was mutated by means of N-methyl-N'-nitro-N-nitrosoguanidine (MNNG), and an amidase-free mutant was isolated having the capability of hydrolyzing D,L-α-aminonitriles only as far as to the stage of the D,L-α-amino acid amides. This mutant was deposited on Oct. 17, 1986 in the "Deutsche Samlung von Mikro-organismen" [German Culture Collection], Grisebachstrasse 8, Göttlingen, Germany, under the number DSM 3875.

With the aid of the novel microorganism Actinetobacter calcoaceticus SM 3875, as well as the previously known microorganisms Arthrobacter sp. ATCC 31 652 or Corynebacterium sp. ATCC 31 662, it is now possible to hydrolyze D,L-α-aminonitriles to L-amino acids without D-amino acid amides remaining as by-products.

Amino acids that can be synthetized by means of the process of this invention are, for example, the amino acids listed in Hoppe-Seyler's "Z. Physiol. Chem." 348:256–261 (1967), as well as their derivatives wherein optionally hydroxy groups, thiol groups, amino groups and carboxy groups present in the residue A according to Formula I are blocked by suitable blocking groups.

With respect to their industrial exploitation, those amino acids are preferred process products of the synthesis according to the invention wherein the residues A have the meanings set forth in claim 4.

Suitable alkyl residues A are those carrying, for example, the methyl group, the ethyl group, the propyl group, the 1-methylethyl group, the butyl group, the 1-methylpropyl group, the 2-methylpropyl group, the 1,1-dimethylethyl group, the pentyl group, the 1-methylbutyl group, the 3-methylbutyl group, or the hexyl group. Especially preferred alkyl groups A are those of maximally 6 carbon atoms, such as the methyl group of the process product alanine, the 1-methylethyl group of valine, the 2-methylpropyl group of leucine, the 1-methylpropyl group of iso-leucine, or the ethyl group of α-aminobutyric acid.

The alkyl groups A can optionally be substituted by hydroxy groups, mercapto groups, amino groups or carbonyl groups, monosubstituted alkyl groups being preferred, or they can be interrupted by oxygen atoms (preferably one), nitrogen atoms (preferably one or two) or sulfur atoms (preferably one). Alkyl groups substituted by hydroxy groups or mercapto groups that deserve special emphasis are the hydroxy-methyl group of serine, the 1-hydroxyethyl group of threonine, the mercaptomethyl group of cysteine, the 2-mercaptoethyl group of homocysteine, and the 1-mercapto-1-methylethyl group of β-thiovaline. A preferred alkyl group A interrupted by a sulfur atom is the 2-methylthioethyl group of methionine. Alkyl groups A carrying an amino group as a substituent are, for example, the 2-aminoethyl group of α,γ-diaminobutyric acid, the 3-aminopropyl group of ornithine, and the 4-aminobutyl group of lysine. Alkyl groups A substituted by carboxy groups can be constituted, for example, by the 2-carboxyethyl group of glutamic acid.

Examples for phenyl residues, benzyl residues or 3-indolylmethyl residues A, substituted by hydroxy groups, are the 4-hydroxyphenyl residue, the 4-hydroxy-phenylmethyl residue and the 5-hydroxy-3-indolylmethyl residue.

The invention concerns the process as characterized in claim 1 for the preparation of L-amino acids of general Formula I from the α-aminonitriles of general Formula II, as well as the process characterized in claim 2 for the preparation of amino acid amides of general Formula III, and the process characterized in claim 3 for the preparation of L-amino acids from these amides.

For performing these processes, the micro-organism utilized is grown under the customarily used culture conditions in a suitable nutrient medium under aeration, in the form of submerged cultures. Then the substrate (preferably dissolved in a suitable solvent) is added to the culture and fermentation is carried out until maximum substrate conversion has been achieved.

Suitable substrate solvents are, for example, water, methanol, ethanol, glycol monomethyl ether, dimethylformamide or dimethyl sulfoxide.

The optimum substrate concentration, time of substrate addition, and fermentation period depend on the structure of the substrate employed and on the type of fermentation conditions adopted. These variables, as is generally necessary in microbiological fermentations, must be determined in the individual case by preliminary tests with which a person skilled in the art is familiar. During fermentation, the pH value of the fermentation broth is preferably set to pH 7.5-10.

On the other hand, however, it is also possible, and frequently advantageous because of the strong polarity of the products of this process, to separate the incubated microorganism from the culture medium, for example by filtration or centrifuging, and to perform the fermentation of the substrates with the isolated cell mass in the resting cell method.

It can furthermore be expected that the process of this invention can also be performed very well by means of immobilized microorganisms.

Immobilization of the microorganisms by embedding in a polymer that does not denature the microorganisms takes place according to methods well known to those skilled in the art. (I. Chibata, Immobilized Enzymes; Research and Development, 1978; S. P. Colowick and N. O. Kaplan, Methods in Enzymology, Academic Press, New York, et al., vol. 44, 1976; and Bo Matthiasson, Immobilized Cells and Orgaelles, CRC Press, Inc., Boca Raton, Florida, vols. 1 and 2).

Suitable immobilized preparations are probably:

Immobilized Microorganisms on Alginate Basis

These can be prepared by suspending the microorganisms in an aqueous prepolymer solution containing 0.5-5% by weight of sodium alginate and introducing this suspension at a temperature of 5°-40° C. under agitation into a 0.01-0.4-molar aqueous solution of an aluminum salt or preferably calcium salt (e.g. calcium chloride).

Immobilized Microorganisms on Carrageenan Basis

These can be prepared, for example, by suspending the microorganisms in a 0.1-1.0% by weight aqueous carrageenan solution heated to 25°-50° C., allowing the solution to cool off until it assumes a gel-like state, mechanically comminuting the gel and then hardening same in a 0.2-2.0% by weight aqueous solution of a potassium salt (e.g. potassium chloride).

Immobilized Microorganisms on Chitosan Basis

These can be produced, for example, by suspending the microorganisms in a 0.5-13% protonated chitosan solution (adjusted to pH 4.5-5.5), heated to 20°-40° C., and adding thereto dropwise a counterion solution of, for example, potassium hexacyanoferrate(II) (with a concentration of 0.01-1 mole/liter).

The process according to this invention as set out in claim 1 can be performed by treating the $\alpha$-aminonitriles of Formula II with the microorganisms in succession or simultaneously. In case the various microorganisms are made to act on the substrates simultaneously, it is advantageous to mix the cells of Actinetobacter calcoaceticus and Arthrobacter sp and/or Corynebacterium sp. in a ratio of 1:2 to 1:20.

EXAMPLE 1

(a) A 500 ml Erlenmeyer flask with 100 ml of a sterile nutrient medium, containing 0.05 g of trisodium citrate
0.35 g of dipotassium hydrogen phosphate
0.01 g of magnesium sulfate heptahydrate
0.1 g of propionic acid amide is inoculated with a culture of Actinetobacter calcoaceticus DSM 3875 and shaken at 180 rpm for 20 hours at 30° C.

The cells are then removed by centrifuging and resuspended in 20 ml of a 0.1-molar potassium phosphate buffer, pH 7.0.

(b) A 500 ml Erlenmeyer flask with 100 ml of a sterile nutrient solution, containing 0.05 g of trisodium citrate
0.35 g of dipotassium hydrogen phosphate
0.15 g of potassium dihydrogen phosphate
0.01 g of magnesium sulfate heptahydrate
0.1 g of ammonium sulfate is inoculated with Arthrobacter spec. ATCC 31 652 and shaken at 180 rpm for 20 hours at 30° C. Then the cells are removed by centrifuging and resuspended in 20 ml of 0.1 -molar potassium phosphate buffer, pH 7.

(c) An amount of 0.5 ml of cell suspension of Actinetobacter calcoaceticus DSM 3875—prepared according to Example (a)—is mixed with 1.5 ml of a cell suspension of Arthrobacter spec. ATCC 31 652—produced according to Example (b)—and combined with 2 mg of D,L-$\alpha$-amino-$\beta$-phenylpropionitrile, and stirred for 4 hours at 30° C. The resultant reaction mixture is tested by thin-layer chromatography and by reaction with L- and D-amino acid oxidase for its content of amino acids. The mixture contains 1.2 mg of L-phenylalanine, but no D-phenylalanine.

EXAMPLE 2

Under the conditions of Example 1, but with the use of Corynebacterium sp. ATCC 31 662 in place of Arthrobacter sp. ATCC 31 652, 2 mg of D,L-$\alpha$-amino-$\beta$-phenylpropionitrile is reacted; by analysis, 1.3 mg of L-phenylalanine is found in the reaction mixture, but no D-phenylalanine.

EXAMPLE 3

(a) Under the conditions of Example 1(b), 100 ml of a culture of Arthrobacter sp. ATCC 31 652 is incubated. The resultant cells are removed by centrifuging and resuspended in 100 ml of 0.1-molar potassium phosphate buffer.

(b) 5 ml of the bacterial suspension is combined with 5 mg of D-phenylalaninamide and stirred at 30° C. for 4 hours. Analysis of the reaction mixture yields 2.1 mg of L-phenylalanine, but no D-phenylalanine.

EXAMPLE 4

(a) Under the conditions of Example 1(b), 100 ml of a culture of Corynebacterium sp. ATCC 31 662 is incubated. The resultant cells are removed by centrifuging and resuspended in 100 ml of 0.1-molar potassium phosphate buffer.

(b) 5 ml of the bacterial suspension is combined with 5 mg of D-phenylalaninamide and stirred at 30° C. for 4 hours. Analysis of the reaction mixture yields 1.8 mg of L-phenylalanine, but no D-phenylalanine.

EXAMPLE 5

Under the conditions of Example 3, 5 mg of D,L-tryptophanamide is reacted, producing 1.5 mg of L-tryptophan, but no D-tryptophan.

EXAMPLE 6

Under the conditions of Example 4, 5 mg of D,L-tryptophanamide is reacted, forming 1.3 mg of L-tryptophan, but no D-tryptophan.

EXAMPLE 7

Under the conditions of Example 3, 5 mg of D,L-leucinamide is reacted, thus obtaining 2.2 mg of L-leucine, but no D-leucine.

EXAMPLE 8

Under the conditions of Example 4, 5 mg of D,L-leucinamide is reacted, forming 2.4 mg of L-leucine, but no D-leucine.

EXAMPLE 9

Under the conditions of Example 3, D,L-alaninamide is reacted, thus producing L-alanine, but no D-alanine.

EXAMPLE 10

Under the conditions of Example 4, D,L-alaninamide is reacted, thus forming L-alanine but not D-alanine.

EXAMPLE 11

Under the conditions of Example 3, D,L-valinamide is reacted, forming L-valine but no D-valine.

EXAMPLE 12

Under the conditions of Example 4, D,L-valinamide is reacted, thus producing L-valine but no D-valine.

EXAMPLE 13

Under the conditions of Example 3, D,L-methioninamide is reacted, producing L-methionine but no D-methionine.

Under the conditions of Example 4, D,L-methioninamide is reacted, forming L-methionine but no D-methionine.

EXAMPLE 15

5 mg of D,L-α-amino-β-phenylpropionitrile is reacted with 5 ml of cell suspension of Actinetobacter calcoaceticus DSM 3875—prepared according to Example 1(a) yielding, according to analysis by thin-layer chromatography, 4 mg of D,L-phenylalaninamide.

EXAMPLE 16

Under the conditions of Example 15, D,L-aminophenylacetonitrile is reacted, forming D,L-phenylglycinamide.

EXAMPLE 17

Under the conditions of Example 15, D,L-α-aminopropionitrile is reacted, producing D,L-alaninamide.

EXAMPLE 18

Under the conditions of Example 15, D,L-α-aminovaleric acid nitrile is reacted, forming D,L-valinamide.

EXAMPLE 19

Under the conditions of Example 15, D,L-α-amino-β-methylvaleric acid nitrile is reacted, thus obtaining D,L-isoleucinamide.

EXAMPLE 20

Under the conditions of Example 15, aminoacetonitrile is reacted, yielding the glycinamide.

In the claims:

1. A process for preparing an L-amino acid of formula I

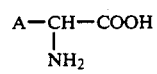  (I)

wherein A is the residue of an amino acid molecule, from a racemic mixture of a D,L-α-aminonitrile of formula II

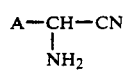  (II)

wherein A has the meaning given above, comprising
fermenting the racemic D,L-α-aminonitrile with a culture of *Actinetobacter calcoaceticus* DSM 3875 and
reacting the thus-obtained racemic mixture of the D,L-α-amino acid amide of formula III

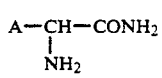  (III)

wherein A has the meaning given above,
with a culture of a microorganism containing an amino acid amide racemase and an L-amino acid amide amidase.

2. A process for preparing an L-amino acid of formula I

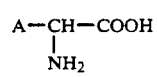  (I)

wherein A is the residue of an amino acid molecule, comprising fermenting a racemic mixture of a D,L-amino acid amide or a D-amino acid amide of formula III

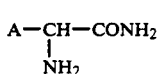  (III)

wherein A has the meaning given above,
with a culture of a microorganism containing an amino acid amide racemase and an L-amino acid amide amidase.

3. A process for preparing an L-amino acid or D,L-amino acid amide according to claim 1, wherein
A is an alkyl residue of 1-12 carbon atoms optionally substituted by a hydroxy group, a mercapto group, a halogen atom, an amino group, or a carboxy group and/or optionally interrupted by an oxygen, nitrogen or sulfur atom; a 4-imidizolylmethyl residue; or a phenyl residue, benzyl residue or 3- indolylmethyl residue, each of which is optionally substituted by a hydroxy group.

4. A process for preparing an L-amino acid according to claim 1, wherein the microorganism containing amino acid amide racemase and L-amino acid amide amidase is one of the species Arthrobacter sp. ATCC 31 652 or Corynebacterium sp. ATCC 31 662.

* * * * *